US010167307B2

(12) United States Patent
Sobolik et al.

(10) Patent No.: US 10,167,307 B2
(45) Date of Patent: Jan. 1, 2019

(54) PROCESS FOR EXTRACTION OF SAPONINS FROM AGRICULTURAL PRODUCTS

(71) Applicant: Minn-Dak Farmers Cooperative, Wahpeton, ND (US)

(72) Inventors: Jeffrey Sobolik, Reynolds, ND (US); Richard Ames, Wahpeton, ND (US)

(73) Assignee: Minn-Dak Farmers Cooperative, Wahpeton, ND (US)

( * ) Notice: Subject to any disclaimer, the term of this patent is extended or adjusted under 35 U.S.C. 154(b) by 0 days.

(21) Appl. No.: 15/218,545

(22) Filed: Jul. 25, 2016

(65) Prior Publication Data

US 2017/0044201 A1  Feb. 16, 2017

Related U.S. Application Data

(60) Provisional application No. 62/197,229, filed on Jul. 27, 2015.

(51) Int. Cl.
 *C07H 15/24* (2006.01)
 *C07H 1/08* (2006.01)
 *C07H 15/256* (2006.01)
 *C07J 63/00* (2006.01)

(52) U.S. Cl.
 CPC ............ *C07H 15/24* (2013.01); *C07H 1/08* (2013.01); *C07H 15/256* (2013.01); *C07J 63/008* (2013.01)

(58) Field of Classification Search
 None
 See application file for complete search history.

(56) References Cited

U.S. PATENT DOCUMENTS

| 6,355,816 B1 | 3/2002 | Dobbins |
| 2016/0376541 A1 | 12/2016 | Ames et al. |

FOREIGN PATENT DOCUMENTS

| CN | 1570131 A | 1/2005 |
| CN | 1740327 A | 3/2006 |
| CN | 101096643 A | 1/2008 |
| CN | 102872319 A | 1/2013 |
| WO | WO 2008/134510 A2 | 11/2008 |
| WO | WO 2009/081211 A2 | 7/2009 |

OTHER PUBLICATIONS

Yangxiao, CN 102617695 A, Aug. 1, 2012, machine translation.*
Search Report and Written Opinion dated Oct. 6, 2016 for PCT Application No. PCT/US16/43859, 11 pages.
Berlowska et al., "Cell lysis induced by membrane-damaging detergent saponins from Quillaja saponaria", Enzyme and Microbial Technology (Jul.-Aug. 2015) vol. 75-76, pp. 44-48. Abstract.
Sadowska et al., "New pharmacological properties of *Medicago sativa* and Saponaria officinalis saponin-rich fractions addressed to Candida albicans", Journal of Medical Microbiology (Aug. 2014) vol. 63, No. Part 8, pp. 1076-1086. Abstract.
Kaczorek et al., "Yeast and bacteria cell hydrophobicity and hydrocarbon biodegradtion in the presence of natural surfactants: Rharnnolipides and saponins", Bioresource Technology (Jul. 2008) vol. 99, No. 10, pp. 4285-4291. Abstract.
Zola, "Lysis of the limiting membrane of Mycoplasma galliseptictum by chemical agents", Journal of General Microbiology (1968). Abstract.
Nilsson, "Uber die Bedeutung der Zellen-struktur fur den harmonischen Verlauf des Stoffwechsels in der Zelle", Arch Mikrobiol (1942) vol. 12, pp. 63. Abstract.
Pourbaix et al., "The liberation from yeast of substances giving the nitroprusside reaction", Biochem Journal (1928) vol. 22, No. 4, pp. 1112-1127. Abstract.
Kofler, "Die Saponine", (1927), Abstract.
International Preliminary Report on Patentability and Written Opinion for International Application No. PCT/US2016/043859, dated Jan. 30, 2018, 7 pages.

* cited by examiner

*Primary Examiner* — Layla D Berry
(74) *Attorney, Agent, or Firm* — Patterson Thuente Pedersen, P.A.

(57) ABSTRACT

A process for the extraction and concentration of saponins from agricultural feedstocks. An agricultural feedstock can undergo a first preparation step intended to increase surface area of the feedstock for increased efficiency in extracting saponin from the feedstock. A saponin extraction step can extract saponin from the prepared feedstock and diffuse the saponin into a solution. A pH adjusted crossflow filtration step can be used to concentrate the saponin into a concentrated saponin solution. One or more pH adjusted centrifugation steps can be used to spin out and concentrate suspended saponin solids. The saponin solids can undergo a drying step to remove any excess water and produce a purified saponin product that can be easily packaged and transported.

10 Claims, 2 Drawing Sheets

PROCESS FOR EXTRACTION OF SAPONINS FROM AGRICULTURAL PRODUCTS

RELATED APPLICATION

The present application claims the benefit of U.S. Provisional Application No. 62/197,229 filed Jul. 27, 2015, which is hereby incorporated herein in its entirety by reference.

FIELD OF THE INVENTION

The present invention relates generally to processes for the extraction of saponins from agricultural products. More specifically, the present invention is directed to processes for extracting and concentrating saponins with membrane(s) and/or other separation systems.

BACKGROUND OF THE INVENTION

Saponins, as chemically illustrated within FIG. 1, are a family of glycoside compounds that are found in a wide variety of plants including, for example, sugarbeets, soybeans, peanuts, various bean species, oats, asparagus, spinach, alfalfa and various tree species. Saponins can be found in high concentrations in portions of the plant that are generally not considered as valuable portions of the plant, for example, in the skin, leaves and roots. Saponins are used in a variety of applications and products including, for example, soaps and foaming agents. In some instances, the presence of residual saponins in other agricultural products, such as, for example, in beet sugar for use with carbonated beverages, can lead to undesirable interactions due to flocculation properties.

More recently, saponins have begun to be investigated for various health properties and as nutritional supplements. For instance, it has been suggested that saponins may possess anti-cancer and cholesterol-lowering benefits as well as being a contributor to the health benefits associated with soybeans and garlic. Due to these believed health benefits, it would be advantageous to develop processes allowing for commercial extraction of saponins.

SUMMARY OF THE INVENTION

Processes according to the present invention allow for the extraction and concentration of saponins from saponin-containing agricultural products. More specifically, processes of the present invention provide for the extraction and concentration of saponins from agricultural by-products. In one representative embodiment, the processes of the present invention are directed to saponin extraction from sugarbeet leaves, roots and skins with no negative impact upon the production of the traditional sugarbeet product, refined white sugar. Processes according to the present invention can be utilized to extract saponin from other agricultural products including, for example, soybeans, peanuts, various bean species, oats, asparagus, spinach, alfalfa and various tree species.

In one aspect of the present invention, an agricultural feedstock can undergo a first preparation step intended to increase surface area for increased efficiency of saponin extraction. Representative preparation technologies can include, for example, grinding, slicing, macerating, crushing and combinations thereof. The invention can further comprise a saponin extraction step whereby saponin is extracted from the prepared feedstock and diffused into a liquid solvent. The saponin extraction step can include pH adjustment and heating to increase extraction efficiency. The filtration process begins with a pre-filtration clarification and a caustic pH adjustment to remove suspended solids such that the filtration step is operated at a pH within a range of about 7.0 to about 12.0. The invention can further comprise of a filtration step in which a concentrated saponin stream is separated from a filtrate steam. The filtrate stream can be returned to the process to increase overall saponin recovery and to reduce water requirements. The invention can further comprise one or more centrifugation steps to spin out and concentrate suspended saponin solids. Any centrate from the one or more centrifugation steps can be recycled to the process to increase saponin recovery and to reduce water requirements. The one or more centrifugation steps can include an acidification step to reduce the saponin stream pH to a range of about 2.0 to about 7.0. The invention can further comprise a drying step to remove any excess water from the centrifuged saponin stream resulting in a dried saponin product that can be easily packaged and transported.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be completely understood in consideration of the following detailed description of various embodiments of the invention in connection with the accompanying drawings, in which.

Figure 1:
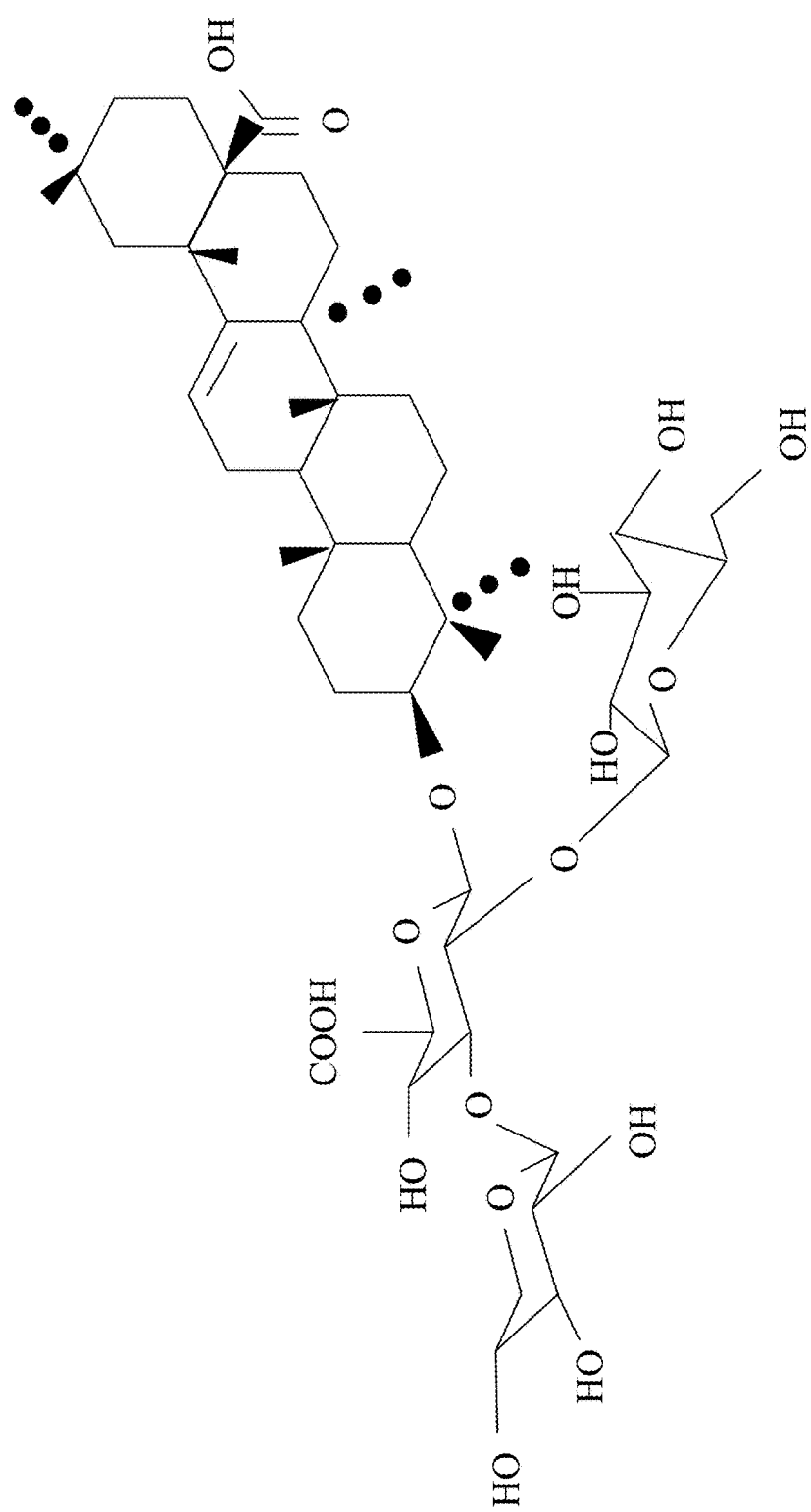
FIG. 1 illustrates a chemical structure of a representative saponin.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

Figure 2:
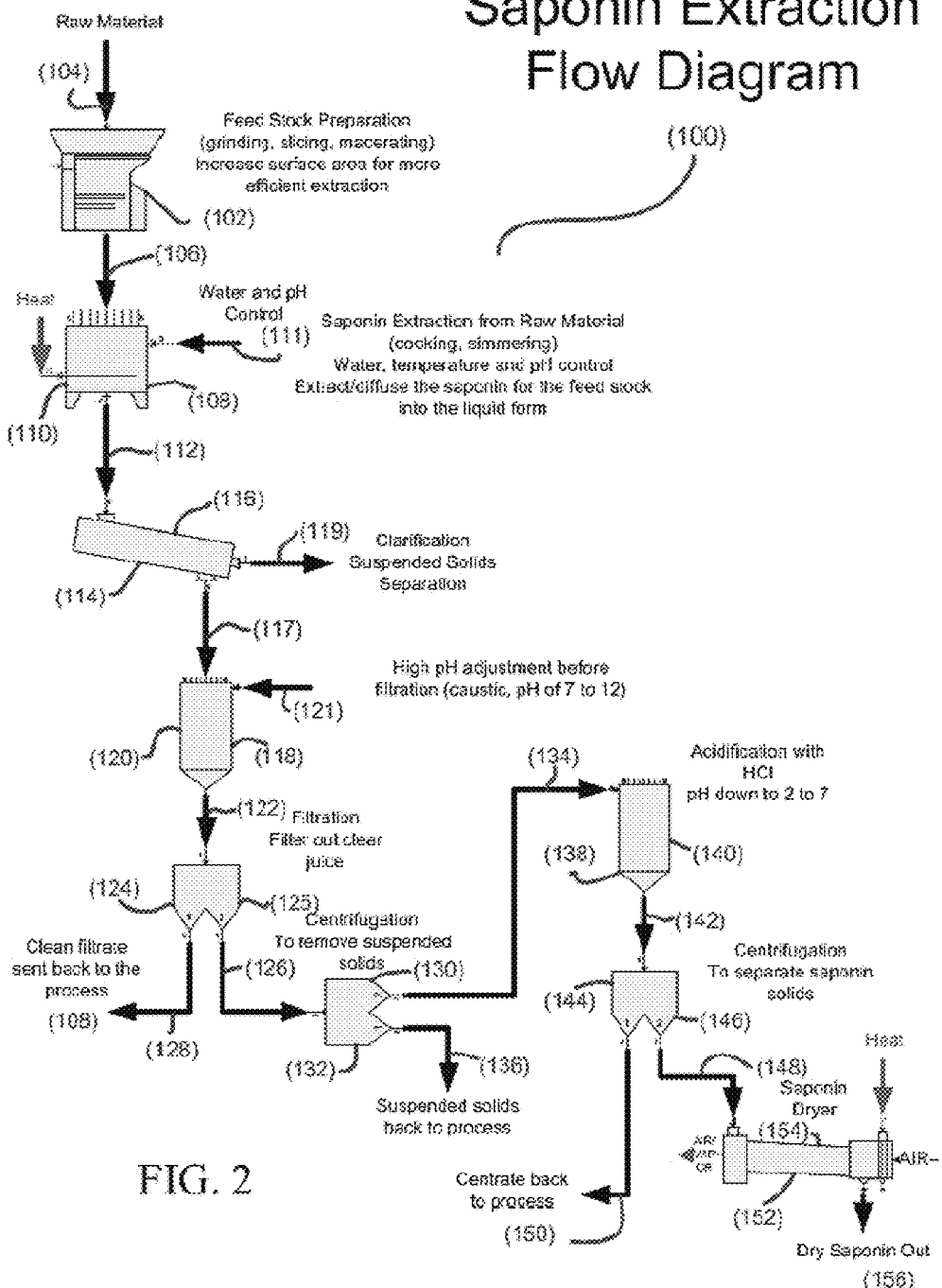
FIG. 2 illustrates a process flow diagram of the extraction of saponin from agricultural products according to an embodiment of the present invention.

An embodiment of a saponin extraction process (100) for use in extracting saponin from agricultural byproducts is illustrated generally in FIG. 2. Saponin extraction process (100) can be utilized with a variety of agricultural feedstocks (104) such as, for example, by-products or waste products, including for example, sugarbeet leaves, skins, and roots. Alternatively, the agricultural by-products (104) can be from agricultural products such as, for example, soybeans, peanuts, various bean species, oats, asparagus, spinach, alfalfa and various tree species.

In a first preparation step (102), an agricultural feedstock (104) is prepared for saponin extraction. Generally, the agricultural feedstock (104) is processed to increase the available surface area to increase saponin extraction efficiency. Preparation step (102) generally comprises physical processing steps for example, grinding, shredding, slicing, macerating, crushing, and combinations thereof. Following preparation step (102), a prepared feedstock (106), having a substantially increased amount of surface area, is ready for further processing.

In a saponin extraction step (108), the prepared feedstock (106) is introduced into a stirred tank (110) into which water (111) is introduced and the resulting solution is heated to a temperature range of 30° C. to 250° C. and allowed to simmer for about 2 to about 600 minutes. Prior to heating, the pH is adjusted by adding acid or base such that the solution has an adjusted pH of about 3 to about 9. During simmering of the solution, saponin is extracted from the prepared feedstock (106) and enters into saponin solution (112).

Saponin solution (112) is next directed into a clarifier (114) in a clarification step (116). Within the clarifier (114), any suspended particles are removed from the saponin solution (112) to form a clarified saponin solution (117) and a suspended solids solution (119).

Next, the clarified saponin solution (117) is directed into a pH adjustment tank (118) in a pH adjustment step (120). Within the pH adjustment tank (118), a base (121), for example sodium hydroxide, is added until the clarified saponin solution has a pH of about 7 to about 12 to form a pH-adjusted saponin solution (122).

The pH-adjusted saponin solution (122) is directed into a filtration system (124) in a filtration step (125). Filtration system (124) preferably comprises a membrane-based cross-flow filtration system for producing a saponin concentrate (126) and a filtered permeate (128). Filtration system (124) can comprise a microfiltration system utilizing a microfiltration membrane having pores sized to remove particulate matter larger than about 0.05 microns to about 0.2 microns. Representative microfiltration membranes can be manufactured of materials such as, for example, PTFE (Teflon®), and are commercially available from companies such as New Logic Research, Inc. of Emeryville, Calif. Generally, the saponins within the pH adjusted saponin solution (122) are too large as measured by molecular weight to pass through the pores such that the saponins are concentrated in the saponin concentrate (126) as water passes through the pores and forms filtered permeate (128). Filtered permeate (128) can subsequently be returned and reused in the saponin extraction process (100) by recycling the filtered permeate (128) back to the saponin extraction step (108). Preferably, the filtration system (124) produces a filtered permeate volume (128) that accounts for 50% to 80% or higher of the pH adjusted saponin solution volume (122). Depending upon recovery levels of the filtration system (124), the concentration of saponin within saponin concentrate (126) can be increased from about 2 to 10 times as compared to saponin concentrations within the pH adjusted saponin solution (122).

Saponin concentrate (126) is directed into a centrifuge (130) in a first centrifugation step (132). Generally, centrifuge (130) causes any suspended solids to be spun from the saponin concentrate (126) to form a first centrifuged concentrated saponin centrate (134) and a first suspended solid stream (136). The suspended solids within the first suspended solid stream (136) can contain saponin such that first suspended solid stream (136) can be recycled, returned and reused in the saponin extraction process (100) to increase the overall recovery of saponin.

Next, the first centrifuged saponin centrate (134) is directed into an acid adjustment tank (138) where an acid (140), for example, HCl is added to the first centrifuged saponin centrate (134) to a pH of about 2 to about 7 to form a reduced-pH saponin centrate solution (142).

The reduced-pH saponin centrate (142) is then directed into a second centrifuge (144) in a second centrifugation step (146). Generally, second centrifuge (144) causes any flocculated saponin-rich solids to be spun from the reduced pH saponin centrate (142) to form a second centrifuged pH saponin rich concentrate (148) and a second saponin lean centrate stream (150). The centrate within the second centrate stream (150) can contain saponin such that second centrate stream (150) can be recycled, returned and reused in the saponin extraction process (100) to increase the overall recovery of saponin.

Finally, the second centrifuged saponin rich concentrate (148) is directed into an air dryer (152) in a drying step (154). Generally, any remaining water within the second centrifuged saponin concentrate (148) is removed to form a dry, purified saponin product (156). The dry, purified saponin product (156) is ready for packaging and use as a saponin supplement or as an ingredient in other saponin-enriched products.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents.

The invention claimed is:

1. A process for extracting saponin from agricultural feedstocks, comprising:
   preparing an agricultural feedstock for saponin extraction from the agricultural feedstock;
   introducing the prepared agricultural feedstock and water into a tank to form a feedstock water solution;
   adjusting the pH of the feedstock water solution to extract a saponin solution in an extraction liquid form;
   clarifying the extraction liquid form to remove any insoluble suspended solids from the saponin solution;
   filtering the saponin solution with a microfiltration member to separate a clean filtrate and a concentrated saponin solution, such that a saponin level within the concentrated saponin solution is concentrated by about 2 to about 10 times as compared to the saponin level in the saponin solution;
   adjusting a pH of the concentrated saponin solution through the addition of an acid such that the pH of an acidified concentrated saponin solution is within a pH range from about 2 to about 7;
   centrifuging the acidified concentrated saponin solution to separate suspended saponin solids from the acidified concentrated saponin solution thereby forming a suspended solid stream and a saponin-rich centrate; and
   drying the suspended solid stream to form a purified saponin product.

2. The process of claim 1, wherein the step of preparing the agricultural feedstock comprises:
   increasing the surface area of the agricultural feedstock.

3. The process of claim 2, wherein the step of increasing the surface area is selected from a group including grinding, slicing, macerating, crushing and or combinations thereof.

4. The process of claim 1, further comprising:
   heating the feedstock water solution.

5. The process of claim 1, comprising:
   clarifying the feedstock water solution to remove any suspended solids from the feedstock water solution.

6. The process of claim 1, further comprising:
adding a base to the saponin solution prior to filtering the saponin solution to form a pH adjusted sapoinin solution having a pH range from about 7 to about 12.

7. The process of claim 1, further comprising:
recycling the clean filtrate for use in the step of introducing the prepared agricultural feedstock and water into the tank to form the feedstock water solution.

8. The process of claim 1, further comprising;
recycling the saponin-rich centrate for use in the step of introducing the prepared agricultural feedstock and water into the tank to form the feedstock water solution.

9. The process of claim 1, further comprising:
centrifuging the acidified concentrated saponin solution to remove flocculated saponin solids.

10. A process for extracting saponin from agricultural feedstocks, comprising:
preparing an agricultural feedstock for saponin extraction from the agricultural feedstock;
introducing the prepared agricultural feedstock and water into a tank to form a feedstock water solution;
adjusting the pH of the feedstock water solution to extract a saponin solution in an extraction liquid form;
clarifying the extraction liquid form to remove any insoluble suspended solids from the saponin solution;
filtering the saponin solution with a microfiltration member so as to separate produce a clean filtrate and a concentrated saponin solution, such that a saponin level within the concentrated saponin solution is concentrated by about 2 to about 10 times as compared to the saponin level in the saponin solution;
adjusting a pH of the concentrated saponin solution through the addition of an acid such that the pH of an acidified concentrated saponin solution is within a pH range from about 2 to about 7;
centrifuging the acidified concentrated saponin solution to separate flocculated saponin solids from the acidified concentrated saponin solution thereby forming a suspended solid stream and a saponin-rich centrate; and
drying the suspended solid stream saponin solids to form a purified saponin product.

* * * * *